US006819785B1

(12) United States Patent
Vining et al.

(10) Patent No.: US 6,819,785 B1
(45) Date of Patent: Nov. 16, 2004

(54) IMAGE REPORTING METHOD AND SYSTEM

(75) Inventors: David J. Vining, Winston-Salem, NC (US); Yaorong Ge, Winston-Salem, NC (US); David K. Ahn, Greensboro, NC (US); David R. Stelts, Silver Creek, GA (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 633 days.

(21) Appl. No.: 09/635,515

(22) Filed: Aug. 9, 2000

Related U.S. Application Data

(60) Provisional application No. 60/147,914, filed on Aug. 9, 1999.

(51) Int. Cl.[7] .............................. G06K 9/00; G06F 17/00
(52) U.S. Cl. ....................... 382/128; 382/180; 382/305; 600/300; 128/922; 707/104.1
(58) Field of Search ......................... 600/300; 128/922; 358/403–404; 382/128–134, 305, 180; 707/104.1

(56) References Cited

U.S. PATENT DOCUMENTS

| | | | |
|---|---|---|---|
| 4,315,309 A | | 2/1982 | Coli |
| 5,115,501 A | | 5/1992 | Kerr |
| 5,148,366 A | | 9/1992 | Buchanan et al. |
| 5,235,510 A | * | 8/1993 | Yamada et al. ............. 600/300 |
| 5,267,155 A | | 11/1993 | Buchanan et al. |
| 5,437,278 A | * | 8/1995 | Wilk .......................... 600/425 |
| 5,452,416 A | | 9/1995 | Hilton et al. |
| 5,463,548 A | * | 10/1995 | Asada et al. ................ 600/300 |
| 5,506,984 A | | 4/1996 | Miller |
| 5,581,460 A | | 12/1996 | Kotake et al. |
| 5,587,833 A | | 12/1996 | Kamentsky |
| 5,666,400 A | | 9/1997 | McAllister et al. |
| 5,704,367 A | | 1/1998 | Ishikawa et al. |
| 5,715,449 A | | 2/1998 | Peters, Jr. et al. |
| 5,740,267 A | | 4/1998 | Echerer et al. |

(List continued on next page.)

FOREIGN PATENT DOCUMENTS

WO  98 16903  4/1998

OTHER PUBLICATIONS

Vining et al. "FREEFLIGHT" Digestive Disease Week and the 100th Annual Meeting of the Gastroenterological Association May 16–19, 1999, Orlando, Fl. Program V.116, N. 4, p. 2.

(List continued on next page.)

*Primary Examiner*—Bhavesh M. Mehta
*Assistant Examiner*—Aaron Carter
(74) *Attorney, Agent, or Firm*—Donald R. Piper, Jr.; Dann, Dorfman, Herrell and Skillman PC

(57) ABSTRACT

A method and system are provided to report the findings of an expert's analysis of image data. The method and system are based on a reporting system that forms the basis of an image management system that can efficiently and systematically generate image reports, facilitate data entry into searchable databases for data mining, and expedite billing and collections for the expert's services. The expert identifies a significant finding on an image and attaches a location:description code to the location of that finding in order to create a significant finding and an entry into a database. Further descriptions of that finding, such as dimensional measurements, audio descriptions, 3D rendered snapshots, etc., may be automatically appended to the finding as secondary attributes of the finding within the database. At the end of the expert's evaluation of the image(s), the system sorts the findings in the database and presents the findings by prioritized categories. The expert edits and approves a multimedia report, which may be delivered to an Internet server for immediate access, archived in the database, sent by automated voice, fax or e-mail to an end-user, or any combination thereof.

193 Claims, 10 Drawing Sheets

U.S. PATENT DOCUMENTS

| | | | | |
|---|---|---|---|---|
| 5,779,634 A | | 7/1998 | Ema et al. | |
| 5,782,762 A | * | 7/1998 | Vining | 600/407 |
| 5,793,969 A | | 8/1998 | Kamentsky et al. | |
| 5,807,256 A | * | 9/1998 | Taguchi et al. | 600/425 |
| 5,825,908 A | | 10/1998 | Pieper et al. | |
| 5,878,746 A | * | 3/1999 | Lemelson et al. | 600/407 |
| 5,920,317 A | | 7/1999 | McDonald | |
| 6,014,581 A | | 1/2000 | Whayne et al. | |
| 6,032,378 A | | 3/2000 | Null | |
| 6,058,322 A | | 5/2000 | Nishikawa et al. | |
| 6,117,073 A | * | 9/2000 | Jones et al. | 600/300 |
| 6,282,305 B1 | * | 8/2001 | Huo et al. | 382/128 |
| 6,292,577 B1 | * | 9/2001 | Takahashi | 382/128 |
| 6,317,617 B1 | | 11/2001 | Gilhuijs et al. | |
| 6,366,683 B1 | | 4/2002 | Langlotz | |
| 6,415,048 B1 | | 7/2002 | Schneider | |
| 6,490,370 B1 | * | 12/2002 | Krasinski et al. | 382/195 |
| 6,551,243 B2 | * | 4/2003 | Bocionek et al. | 600/300 |
| 2002/0004798 A1 | | 1/2002 | Babula et al. | |

OTHER PUBLICATIONS

Vining et al., "New Paradigm for Virtual Colonoscopy Processing and Reporting" and "New Paradigm for Digital Image Reporting", 1999 Scientific Program Radiological Society of North America 85th Scientific Assembly and Annual Meeting, Supplement Nov. 1999, V 213 (P), p. 577 and p. 579.

Langlotz, G.P. MD, PhD, "A Graphical Speech–guided Structured Reporting System", 1999 Scientific Prograam Radiological Society of North America 56th Scientific Assembly and Annual Meeting, Supplement Nov. 1999, V213 (P), p. 578.

eDict System, Inc., "www.edictation.com" printed Website on Nov. 21, 2000.

Wheeler, et al., "The John Hopkins Radiology Reporting System", Radiology 119:315–319, May 1976.

Bluemke, et al., "An Automated Radiology Reporting System That Uses HyperCard", Computers in Radiology, AJR 1993; 160:185–187 0361–803X/93/1601–0185 American Roentgen Ray Society, Jul. 23, 1992.

Mani, et al., "A Computer–Assisted Radiologic Reporting System", Radiology 108:587–596, Sep. 1973.

Pendergrass, et al., "An On–Line Computer Facility for Systematized Input of Radiology Reports", Radiology 1969; 92:709–713.

Langlotz, "Enhancing the Expressiveness of Structured Reporting Systems", Journal of Digital Imaging, vol. 13, No. 2, Suppl. 1 (May), 2000: pp 49–53.

Bell, D.S.., et al., "Evaluation of UltraSTAR: Performance of a Collaborative Structured Data Entry System", 1994, AMIA, Inc.; Symposium Supplement 216:222.

Campbell, K.E., et al., "A Computer–Based Tool for Generation of Progress Notes", 1993; Symposium Supplement 284–288.

Dockray, Karl T., "Solo Practice Management: Value of a Computerized Reporting System", Computers in Radiology, JR 1994, 162:1439–1441.

Friedman, C., et al., "A Schema for Representing Medical Language Applied to Clinical Radiology", Journal of the American Medical Informatics Assoc., vol. 1, No. 3, May./Jun. 1994, 1:233–248.

Hundt, W., et al., "A Computer–based reporting system in radiology of the chest", European Radiology, 8, 1002–1008 (1998), Springer–Verlag 1998, 8:1002–1008.

Poon, A.D., et al., "PEN–Ivory: The Design and Evaluation of a Pen–Based Computer System for Structured Data Entry", Stanford University School of Medicine, Journal of the American Medical Informatics Assoc., 1994; (Symposium Supplement) 447–451.

Puerta, A., et al., "Towards a General Computational Framework for Model–Based Interface Development Systems", Stanford University, Proceeding of the International Conference on Intelligent User Interface Design, Calif. 1999.

Jost, "Radiology Reporting", Radiologic Clinics of North America—vol. 24, No. 1, Mar. 1986.

Brolin, "MEDELA: An Electronic Data–Processing System for Radiological Reporting", Radiology 103:249–255, May 1972.

Barnhard, et al., "Computer Autocoding Selecting and Correlating of Radiologic Diagnostic Cases", Apr. 1966, pp. 854–863.

Bell, et al., "Experiments in Concept Modeling for Radiographic Image Reports", J Am Med Informatics Assoc., 1994, 1:249–262.

Kahn, Jr., et al., "Structured Entry of Radiology Reports Using World Wide Web Technology", RadioGraphics 1996; 16:683–691, RSNA, 1996.

Leeming, et al., "Advances in Radiologic Reporting with Computerized Language Information Processing", Radiology 133:349–353, Nov. 1979.

Dietrich, "Knowledge–Based Computer–Assisted Diagnosis of Chest Radiographs", Radiologic Clinics of North America—vol. XVI, No. 3, Dec. 1978.

"The ACR Breast Imaging Reporting and Data System (BI–RADS®)", Copyright © 1994–2002 American College of Radiology, Revised Jun. 1, 2000.

Chronaki, C. et al., "I2Cnet Medical Image Annotation Service", Medical Informatics, Online!, vol. 22, No. 4, 1997, pp. 337–347.

* cited by examiner

New Paradigm Report

Wake Forest University / Baptist Medical Center

| | | | |
|---|---|---|---|
| Patient Name: | DOE, JOHN | Radiologist: | VINING, DAVID |
| Patient ID: | 12345678 | Referring Physician: | WELBY, MARCUS |
| Requisition #: | 87654321 | | |
| Sex: | Male | Date of Exam: | 10/19/1998 |
| DOB: | 1/1/1942 | Date of Report: | 11/3/1998 |

Indication: Colon cancer screening (V76.49)

Patient Prep: Liquid diet, split-dose Fleets Phospho-soda, Gastroview, CO2 insufflation.

Technique: Virtual colonoscopy protocol - CT abdomen (CPT 74150), CT pelvis (CPT 72192), 3D reconstruction (CPT 76375)

Findings

Lungs: Normal.

Liver: Normal.

Spleen: Normal.

Pancreas: Normal.

Gallbladder:

Finding 1: Gallbladder: calculi (ACR 762.81)
        *Exam:* 999, *Series:* 5, *Acquisition:* 1, *X,Y,Z:* -82.3, -36.3, -76.9

Features: *Status:* Recommend clinical correlation
        *Characteristics:* multiple gallstones
        *Size:* 8 mm
        *Voice:* [click for voice description]

Images:

Fig. 7A

Images: 

Adrenals:    Normal.

Kidneys:     Normal.

Colon:

Finding 1a:    Colon, rectum: adenomatous polyp (ACR 757.3111)
                        Exam: 999, Series: 5, Acquisition: 1, X,Y,Z: 26.8, 19.2, -367.9
    Features:      Status: HIGH Priority - Requires surgical attention
                        Characteristics: polypoid, located on left wall, surrounded by fluid
                        Size: 10 mm
                        Voice: [click for voice description]
    Images: 

Finding 1b:    Colon, rectum: adenomatous polyp (ACR 757.3111)
                        Exam: 999, Series: 5, Acquisition: 2, X,Y,Z: 337.1, 354.9, -161.3
    Features:      Status: HIGH Priority - Requires surgical attention
                        Characteristics: polypoid, located on left wall
                        Size: 10 mm
                        Voice: [click for voice description]
    Images: 

Fig. 7B

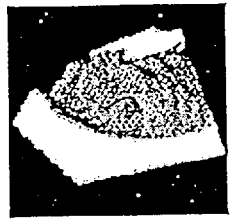

Skeleton:

Finding 1: Lumbosacral spine: degenerative joint disorder (ACR 33.77)
Exam: 999, Series: 5, Acquisition: 1, X,Y,Z: -27.7, 38.2, -272.9

Features: *Status:* n/a
*Characteristics:* minimal hypertrophic changes
*Size:* n/a
*Voice:* [click for voice description]

Images: 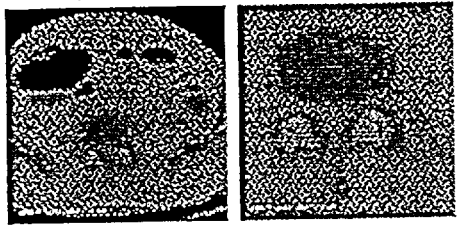

Misc:

Finding 1: Abdominal aorta: atherosclerosis (ACR 981.721)
Exam: 999, Series: 5, Acquisition: 1, X,Y,Z: 9.1, -25.0, -177.9

Features: *Status:* n/a
*Characteristics:* minimal atherosclerosis
*Size:* n/a
*Voice:* [click for voice description]

Images: 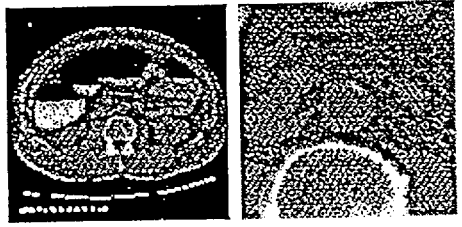

Fig. 7C

IMAGE REPORTING METHOD AND SYSTEM

Applicants claim the benefit of priority to U.S. Provisional Application 60/147,914, filed on Aug. 9, 1999, the contents of which are incorporated herein by reference.

FIELD OF THE INVENTION

The present invention relates generally to an image reporting method and system and more particularly to a method and computer-implemented procedure for creating electronic, multimedia reports based on a new reporting paradigm.

BACKGROUND OF THE INVENTION

Image reporting as currently practiced suffers from a lack of standardization, consistency, accountability, and efficiency. A root cause of these problems is the manner in which reports are generated, beginning with the lack of a standardized report format, particularly in the medical field of radiology.

Radiologists generally review images of a body structure and dictate narrative descriptions of their image findings followed by summary statements. Transcriptionists then transcribe the dictated statements and either print applicable reports or enter such information into a computerized radiology information system (RIS). As a result, the content and format of radiology reports often vary greatly depending on the differing preferences and styles of individual radiologists. This inconsistency among the radiologists' reporting styles often hinders the correlation of the reported findings with the actual images by the recipients of the reports. Variability in the reporting styles also impedes on-going monitoring of specific findings from different examinations on the same patient, a task that is critical for patient care and time-consuming for radiologists. Further, traditional radiology reporting practices do not support data mining, a powerful tool which is useful in clinical trials, epidemiology studies, and outcomes analyses.

In addition, conventional reporting practices often provide no mechanism to allow the radiologist to account for the effective communication of critical report information to the recipient. Frequently, radiologists mistakenly assume that when a report is approved and sent to a referring medical professional, their responsibility ends. To the contrary, however, radiologists are often held accountable for ensuring that proper action is taken on significant findings and are held liable for malpractice when proper action is not taken.

Clinicians are the typical end-users of reports from radiologists. A major complaint of such clinicians against radiologists and their reporting practices involves point of service. This problem is illustrated by the following scenario: a patient receives emergency room x-rays for an injury during the night; a radiologist interprets the x-ray images the next morning; and, following transcription, a report is finally delivered to the emergency room physician, but typically only after the patient has been treated and released. Clinicians are now demanding that radiologists issue reports immediately after an imaging study has been performed.

Hence, there is a pressing need to provide a reporting system which offers a standardized report format, enables consistency among reports, accounts for effective information flow, provides for quick turnaround of information to the end-user, and supports data mining for public health statistics. In addition, these needs extend beyond the field of radiology, and include other medical fields such as pathology, cardiology, dermatology, as well as other image analysis fields such as satellite imagery and photography.

SUMMARY OF THE INVENTION

The present invention relates to a new reporting method and system for reporting the findings of an expert's analysis of image data and, more specifically, to a computer system and computer-implemented method for reporting an expert's findings relative to an analysis of image data. The method and system are based on a new reporting paradigm. The paradigm forms the basis of a radiology practice management system that can efficiently and systematically generate radiology reports, facilitate data entry into searchable databases, support clinical trials and outcomes analyses, and expedite hospital billing and collections. One fundamental aspect of this paradigm is that an expert, e.g. a radiologist, identifies a diagnostically significant feature on an image and attaches a location:description code, or in the case of radiology an anatomical:pathological code, to the location of that feature in order to create a finding, or in the case of radiology a diagnostic finding. The anatomical:pathological code includes the anatomical location followed by a pathological description. Optionally, further attributes of that finding, such as dimensional measurements (e.g., length, area, and volume), audio descriptions, 3D rendered snapshots, etc., may be automatically appended to the diagnostic finding as secondary attributes of the diagnostic finding. All of this information is automatically captured in an intuitive workflow scheme transparent to the expert, and stored in a database. The expert may continue to identify additional diagnostically significant features and create diagnostic findings in any order. At the end of the expert's evaluation of the image(s), the system sorts the diagnostic findings by selected or predetermined categories. In a medical field, these predetermined categories may be anatomical categories. The diagnostic findings are further prioritized by the severity of the diagnosis in order to alert the report recipient, e.g., a clinician. The expert can edit and approve a multimedia report, which may be delivered to an Internet server for immediate access, sent to a database, sent by automated voice, fax or e-mail to the clinician, or any combination thereof. The radiologist can sign the report by electronic or voice signature. The final report presentation may be further customized to satisfy the needs of the clinician.

The reporting system of the present invention is applicable to several other image-based fields including pathology, cardiology, dermatology, satellite imagery, and photography.

BRIEF DESCRIPTION OF THE DRAWINGS

The foregoing summary and the following detailed description of the preferred embodiments of the present invention will be best understood when read in conjunction with the appended drawings, in which:

FIGS. 6 illustrates the user-interface of the present invention in which FIGS. 7A–7C illustrate a selected report of the present invention.

DETAILED DESCRIPTION OF THE INVENTION

Figure 1:
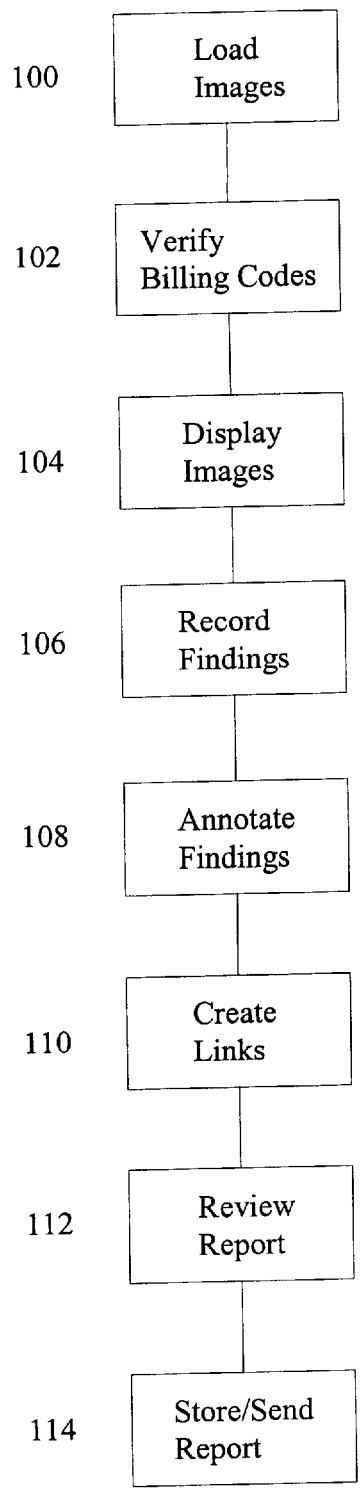
FIG. 1 illustrates a flowchart representing a general method in accordance with the present invention for creating an image report.
Figure 2:
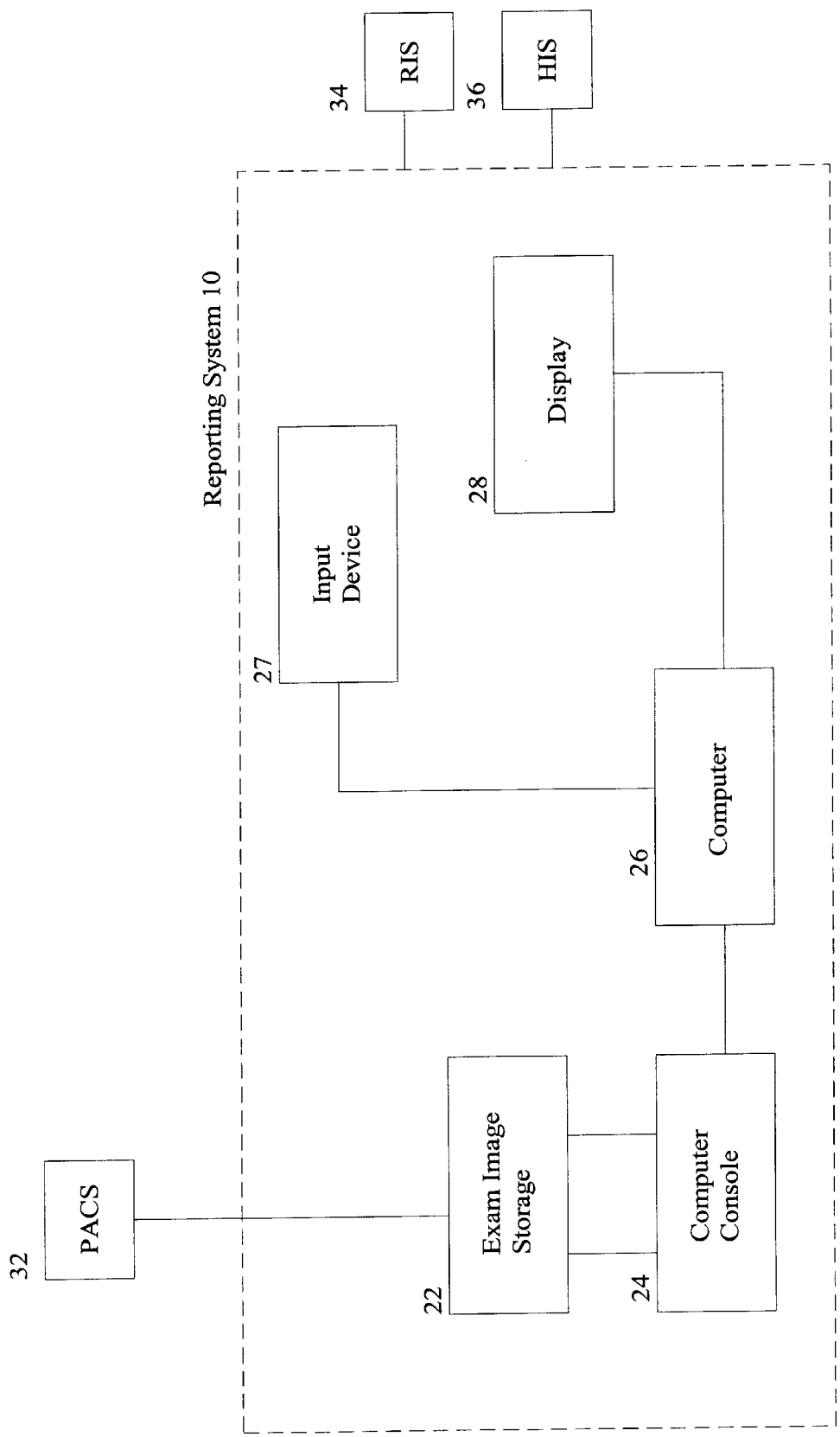
FIG. 2 illustrates a block diagram of a computer system used in the computer-implemented method of the present invention.

A method and system are provided for generating and communicating reports containing an expert's analysis of image data as generally depicted in FIGS. 1 and 2. In addition, a computer-implemented method and a computer system function to create a database of the expert's findings from which a report is generated and from which data mining and other analyses may be conducted. The database can be a computer searchable database and may be a relational computer database.

The method and system of the present invention are applicable to any field which relates to an expert's analysis of images. In particular, however, the method and system of the present invention are well-suited to image analysis found in medical applications. As such, the method and system of the present invention are illustrated in the accompanying figures and description in terms of the medical field of radiology.

The method and system are particularly well-suited to the analysis of digital images. However, the method and system may also be adapted for use with analog images such as conventional x-ray films. For example, the system can utilize a digital camera to load a digital representation of an analog image into computer memory for further processing.

The computerized reporting system 10 is designed to interface with existing information systems such as a Hospital Information System (HIS) 36, a Radiology Information System (RIS) 34, and a Picture Archiving and Communication System (PACS) 32. The reporting system 10 includes an examination image storage 22, a computer console 24, a computer 26, display(s) 28, and an input device 27. For illustration purposes the input device 27 is a three-button computer mouse, where the left and middle-mouse buttons (LMB, MMB) are used, for example, to manipulate image data, and the right-mouse button (RMB) is used, for example, to identify a new diagnostically significant feature and to start a database recording process. Other known input devices including LCD graphics tablets and touch-screens may be used as well as other custom devices. For example a intelligent view box and digital camera device can be used with conventional x-rays.

Bidirectional communication between the reporting system 10 and the information systems 32, 34, 36 allows the reporting system 10 to retrieve data from the such information systems 32, 34, 36 and to update information in these systems to provide the desired report generated by the reporting system 10. For example, the reporting system 10 may download image data corresponding to radiological examinations of patients from the PACS 32. The PACS 32 stores information according to existing standards such as "Digital Imaging and Communications in Medicine" (DICOM). The data from the PACS 32 is stored in the examination image storage 22 where it can be accessed via the computer console 24 and computer 26 for display on the display 28. Alternately, the reporting system 10 can directly access the PACS images without the need for an intermediate storage device, such as image storage 22. Additionally, the reporting system 10 may be linked to communication systems such as the Internet, e-mail systems, fax, telephone, wireless communications systems such as pagers and cellphones, and other communication systems.

Figure 3:
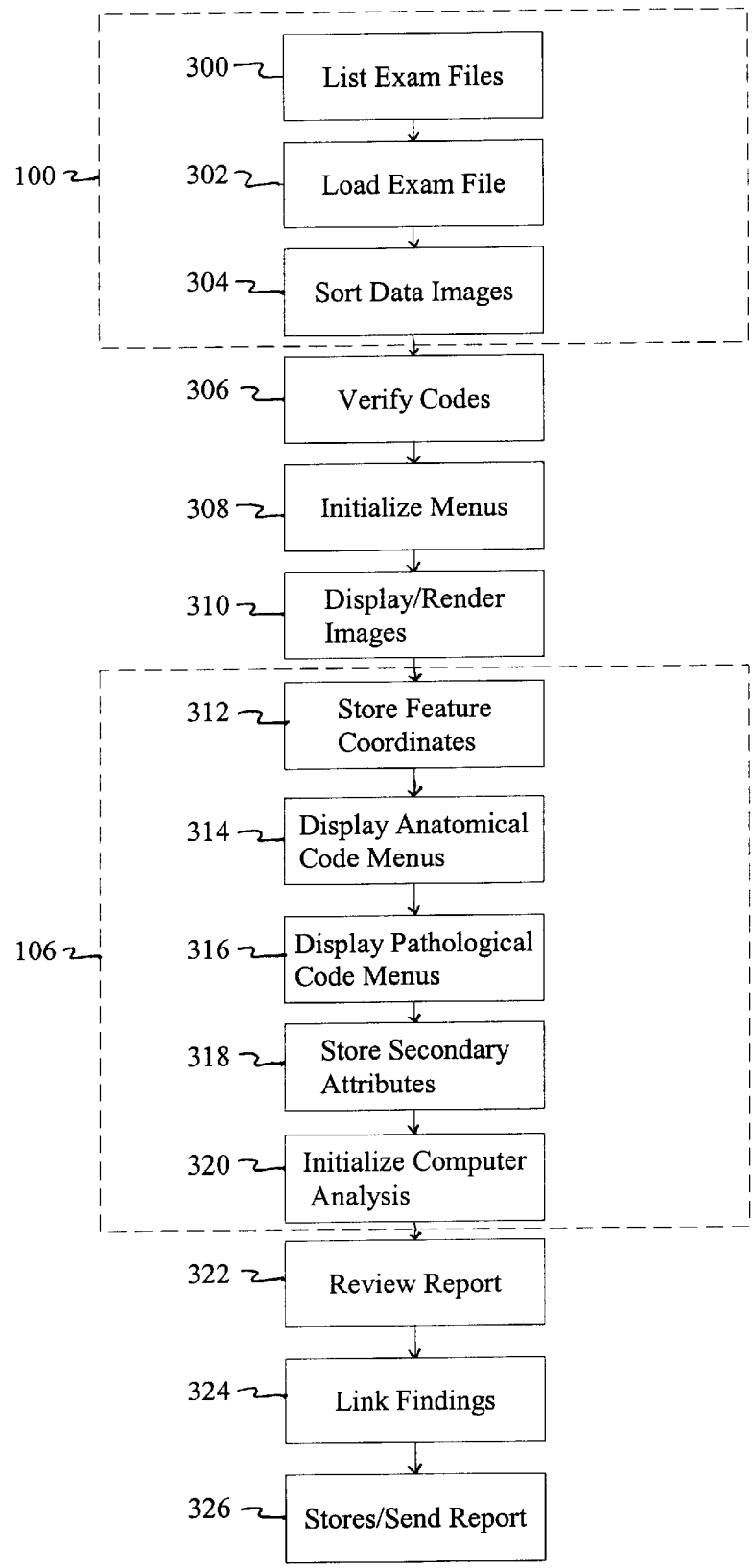
FIG. 3 illustrates a flowchart representing the steps of the process for creating an image report.

Referring now to FIGS. 1 and 3 which illustrate the general method and detailed process steps of the present invention, respectively, preparation of a report begins with the loading of patient data, including billing, demographics, and image data, step 100. A file loader from computer 26 searches the examination storage 22 for examination data files available for analysis and displays the corresponding names of patients in a user-interface at step 300. Upon selection of a particular patient by the radiologist, the file loader displays all of the associated unread examination files for that patient. The radiologist selects a particular examination file, and the file loader loads the corresponding data into computer memory at step 302. The file loader searches through the image data in the selected examination and organizes the images by DICOM series (or any additional subdivisions),at step 304, prior to display in 2D, and optional 3D, viewers.

The file loader also displays the Current Procedural Terminology (CPT) and International Classification of Diseases (ICD) codes assigned to the selected examination and determines if they correlate at steps 102 and 306. (CPT codes describe the type of radiologic examination, and ICD codes indicate the reasons for performing a particular examination.) Proper matching of these codes are often essential for reimbursement by health care insurers. The file loader compares the ICD and CPT codes and displays an alert if the codes are incompatible. The radiologist verifies the codes and enters any necessary changes. Correct assignment of these codes at the beginning of an examination is effected by the reporting system 10 to intelligently guide the presentation of diagnostic code menus during the annotation process described below. Prior to the review process, an anatomical-location menu and a pathology-description menu are initialized using the CPT codes at step 308. Likewise, a series menu is initialized to list all of the DICOM series available in the selected examination file at step 308. In addition, the file loader retrieves existing "new paradigm" reports, i.e., those created using the present invention, from the patient's previous examinations and makes them available for review during the current study.

Figure 6A:
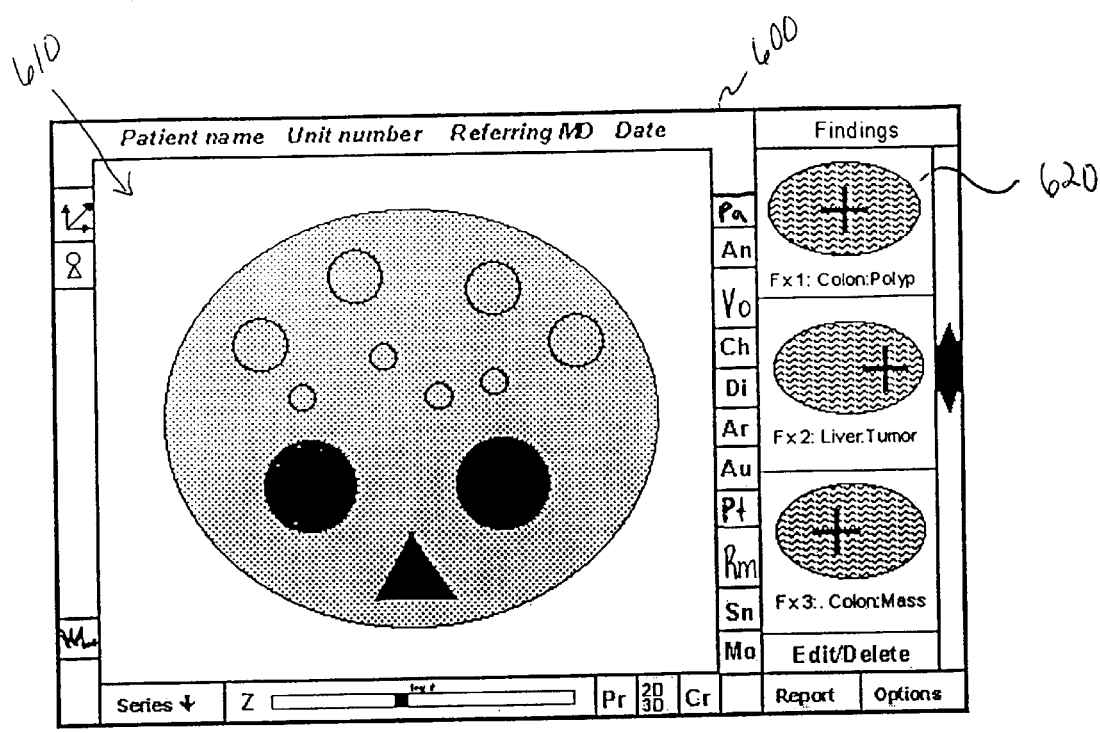
FIG. 6A shows a 2D viewer and FIG. 6B shows a 3D viewer.

After initialization of the menus, the first available image from the sorted images is displayed in a user-interface by a 2D viewer 610 as shown in FIG. 6A from which the radiologist may begin analysis of the first image, at steps 104 and 310. Alternately, the radiologist is free to select a different DICOM series for evaluation from the series menu. For example, a CT or MRI examination often consists of multiple series, whereas a chest x-ray may contain only one series. Two or more series may also be displayed simultaneously (e.g., supine and prone series of a virtual colonoscopy study). A window/level menu, W/L, is available as part of the user-interface which lists preset window and level settings (i.e., grayscale settings) for the 2D viewer. The preset settings can be specified in an options menu.

The step of displaying and rendering images, step 310, includes altering the display of the images in response to commands from the radiologist. For example, the radiologist can pan through a number of images in the 2D viewer as the mouse is moved and the LMB is pressed, provided that more than one image is contained in the series. Similarly, the 2D viewer can translate (i.e., move) the image up/down and sideways when the mouse is moved and the MMB is pressed. The 2D viewer can also zoom the image display when the mouse is moved and the LMB and MMB are pressed simultaneously. An overview button is provided in the user-interface to re-center the image in case the scene is moved out of sight. However, re-centering may be unnecessary if the ability to move or zoom an image is restricted.

Figure 6B:
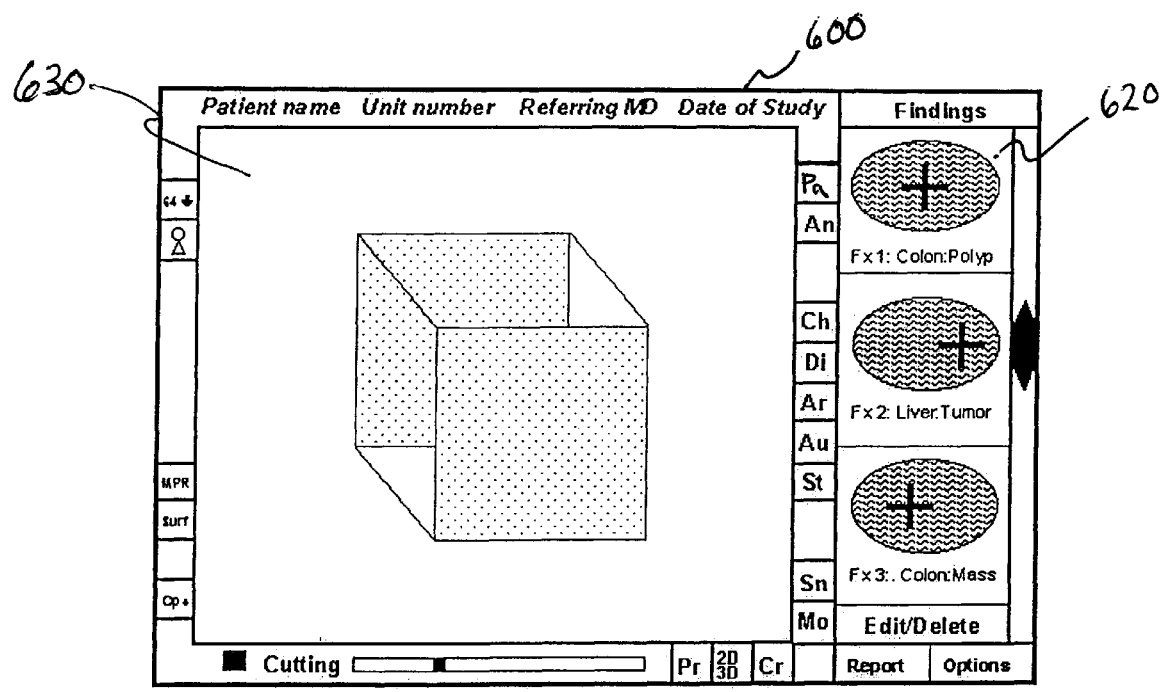

A 3D viewer is also provided in the user-interface, as shown in FIG. 6B to render images in step 310. A 2D/3D toggle button is also included in the user-interface to allow the radiologist to toggle between the 2D and 3D viewers at step 310. In the 3D viewer, the mouse operations are similar to those of the 2D viewer except that pressing the LMB while moving the mouse causes the 3D rendered scene to rotate in space. The LMB can also be used to control a "fly-through" mode as used in virtual endoscopy as disclosed in U.S. Pat. No. 5,782,762.

The 3D viewer incorporates techniques including render around a point and hybrid rendering (i.e., combined volume rendering, surface rendering, and multiplanar [MPR] display). These techniques are the subjects of previous U.S. Pat. Nos. 5,782,762 and 5,920,319, the disclosures of which are incorporated herein by reference. When surface rendering and MPR are utilized, identification of new diagnostically significant features, discussed below, within the 3D environment works in the same fashion, with a RMB click. When the 3D viewer is activated after a diagnostic finding has been created, the volume-rendered image, e.g., a cube of CT data, (or surface-rendered or MPR image(s) ) is centered around the coordinates of the diagnostic finding.

A render-box-size menu is also provided in the user-interface to control the size of the volume (i.e., cube of digital data) rendered in the 3D viewer. When changing the volume size, the 3D display automatically adjusts the scene to fill the screen. An opacity-map menu, Op, in the 3D viewer permits the radiologist to control the level of transparency and grayscale/color scale of a 3D volume rendering.

As a further aspect of the display step 310, an orientation button is provided in the user-interface to allow the radiologist to properly set the orientation of the image data prior to 3D rendering. For example, it is assumed that the 2D first image in a CT series is the most superior (i.e., highest) image, the patient's left is on the radiologist's right, and the patient's anterior surface is facing up. If the series needs to be reoriented, the radiologist can pan through the collection of images to locate the most superior image (or close to it). The radiologist then toggles the orientation button, at which time the 2D viewer goes into an orientation mode. The radiologist freely rotates the image plane by pressing the LMB and moving the mouse until the proper anterior/posterior and left/right orientation is achieved. Finally, the radiologist toggles the orientation button again to set the proper orientation. The 3D viewer then automatically adjusts the image plane so that it is orthogonal to the radiologist's viewpoint. The 3D scene can also be automatically annotated with labeled 3D axes to assist in the visual orientation by the radiologist.

The volume-rendered image can be manipulated in various ways (i.e., using opacity maps, cutting planes, rotation, and fly-throughs). A second method for switching between the 2D and 3D viewers is to click on a 2D thumbnail image representation of a diagnostic finding (or its appended secondary 2D and 3D images) shown in an intermediate report display, thereby recalling the last state of the 2D or 3D viewer associated with the newly activated finding.

When transitioning between 2D and 3D viewers, the last state of each viewer is stored. For example, the proper grayscales (or color scales) and opacity maps are applied according to the last recalled W/L or Op settings, respectively. Similarly, when jumping to a previous finding by clicking on its thumbnail image representation, the last W/L and/or Op settings for that finding are recalled depending on whether the thumbnail represents a 2D or 3D image. A previous button, Pr, allows the radiologist to toggle between the two most recent W/L settings or Op settings in the 2D and 3D viewers, respectively. Alternatively, the user can press on the LMB followed by a click of the RMB to activate the Pr function.

During review of an image using the viewers as described above, the radiologist searches for any diagnostically significant image features. When the radiologist locates a diagnostically significant feature, the radiologist begins the process of recording a diagnostic finding at steps 106 and 312. The process of recording a diagnostic finding begins with positioning the cursor over the location of the feature on the digital image and clicking the RMB at step 312. Alternatively, when applying the invention to conventional x-rays or images, a digital camera device can be pointed at an image finding, and a representative digital image can be recorded. Alternatively, the radiologist may point at the feature by using an intelligent view box. Clicking on the RMB stores the image coordinates, for example DICOM coordinates, and an image number corresponding to the cursor location in a database. To complete the definition of a diagnostic finding, an anatomical:pathological code and, optionally, secondary attributes are assigned to the image coordinates and automatically stored in the database. The anatomical code identifies the anatomical location within the body, and the pathological code describes the pathology of the identified feature. The anatomical:pathological codes may be derived from a predefined lexicon, such as the American College of Radiology (ACR) Index of Radiological Diagnoses or Systematized Nomenclature of Medicine (SNOMED). The secondary attributes provide additional descriptions of the finding and include, for example distance, area and volume measurements, characteristics and status of the finding, as well as multimedia information such as audio descriptions, 3D snapshots, and 3D illustrated movies.

In response to the RMB click the reporting system can automatically display the anatomical-location menu at step 314. The anatomical-location menu may consist of a cascading list of anatomical location codes that have been customized based on the previously verified CPT and ICD codes; i.e., the anatomical-location menu presents only the anatomical organs associated with a particular radiologic examination. The cascading anatomical-location menu provides greater levels of detail of the finding's anatomical location with each cascading level presented. For example, a first level might specify "Gastrointestinal System", a second level "Colon", and a third level "Sigmoid Colon". Upon selection of an anatomical code, the reporting system displays a cascading pathology-code menu, at step 316, which displays a cascading list of pathology codes that correspond to the selected anatomical location. For example, a first level of the pathology-code menu might specify "Neoplasm", the second "Benign Neoplasm", and the third "Polyp". An anatomical:pathological code must be assigned to any unlabeled findings prior to final report approval; otherwise, these findings are labeled with the default "unknown location:unknown pathology" or any combination thereof. When a diagnostic finding has an indeterminate etiology, the radiologist my assign a list of diagnostic possibilities, representing a differential diagnosis, as secondary attributes of that finding. Alternately, the reporting system 10 can incorporate voice activated control and natural language processing in conjunction with or instead of the annotation menus, i.e. the anatomical-location and pathological-description menus. The radiologist could speak "Sigmoid Colon Polyp" to achieve the same result as using the annotation menus.

As each diagnostic finding is created, a representative thumbnail image 620, as shown in FIG. 6, may be displayed on the right side of the 2D and 3D viewers (or on an independent display monitor) for immediate presentation and recall, and the thumbnail images later may be incorporated into the final report. Alternately, the report can be displayed on a second monitor as it is being created. The above method for entering an anatomical:pathological code is denoted "click and label". Two alternative methods are also possible for performing steps 314 and 316.

The first alternative method, "click-pause-label", allows the radiologist to postpone assignment of an anatomical:pathological code until sometime later during the analysis of the finding. In this case, the radiologist must deliberately press anatomy-location and/or pathology-description button, An and Pa, on the 2D or 3D viewer, as shown in FIG. 6, to subsequently activate the corresponding annotation menu. The second alternative method, "click-click-click and label-label-label", allows the radiologist to annotate the diagnostic findings during final report editing. A more detailed description of these two methods is discussed below in conjunction with the method of operation of the reporting system.

The method of entering and annotating diagnostic findings is not limited to computer pull-down menus containing preselected terminology. Keyboard, voice recognition, macros, and natural language processing are available to enter diagnostic findings and secondary attributes.

After assignment of the anatomical:pathological codes, secondary attributes may added at step 318 to embellish or support the diagnosis. As shown in FIG. 6, the user-interface 600 of the reporting system 10 includes various options for adding secondary attributes. A chart of the symbols used on FIG. 6 are set forth in the following chart:

| An | Annotation menu listing ACR Dx codes |
|---|---|
| Vo | Volume measurement button |
| Ch | Characteristic button |
| Di | Distance measurement button |
| Ar | Area measurement button |
| Au | Audio record button |
| Pt | Priority button |
| Rm | Recommendation button |
| Sn | Snapshot button |
| Mo | Movie button |
| W/L ⬇ | Window/Level presets menu |
| ↻ | Orientation button |
| ⚲ | Overview button |
| Pr | Previous window/level setting toggle button |
| 2D/3D | 2D/3D viewer toggle button |
| Cr | Cursor on/off toggle button |
| Series | Series menu |
| MPR | Multi-planar button |
| Surf | Surface rendering button |
| Op ⬇ | Opacity map presets |
| 64 ⬇ | Render box size menu |
| ■ | Opaque cutting plane toggle button |

For example, a characteristics button, Ch, is included to activate a menu of descriptive attributes that enhance a specific diagnostic code set, (i.e., anatomy:pathology code combination). For example, "liver:metastatic neoplasm from colon" (ACR diagnostic code 761.3375) can be further characterized with the number of lesions (i.e., single or multiple).

A distance-measurement button, Di, is included in the user-interface of the reporting system 10 to permit the radiologist to measure a finding in the 2D or 3D viewer with any number of diameters. Similarly, an area-measurement button, Ar, allows the radiologist to define a region-of-interest (ROI) from which the cross-sectional area, mean voxel value, and standard deviation of voxel values in that region can be calculated. Measurements automatically become secondary attributes of the active diagnostic finding and are stored in the database associated with the diagnostic finding. Additionally, a volume-measurement button, Vo, is provided to permit the radiologist to define a volume-of-interest VOI. The reporting system 10 can create the VOI by 3D segmentation means, as disclosed in U.S. Pat. No. 5,782,762, 5,920,319, and 6,083,162, each of which are incorporated herein by reference. A volume measurement calculated from the VOI may be added as a secondary attribute.

The reporting system also permits the assignment of both priority levels and recommendations to a finding. A priority button, Pt, permits the radiologist to add a certain level of significance to a diagnostic finding as a secondary attribute. A recommendation button, Rm, can be used to label a "leaking aortic aneurysm" diagnostic code with "High Priority—Requires immediate attention." By default, the reporting system 10 does not assign any particular priority or recommendation to a diagnostic finding; however, certain diagnostic codes may automatically receive priority and recommendation codes.

An audio button, Au, is included in the user-interface to allow the radiologist to dictate a verbal description of a diagnostic finding, and that audio file becomes a secondary attribute of the finding. The audio file can be saved in the final report unchanged, or it can be transcribed to text by a typist or a voice recognition system.

A snapshot button, Sn, in the user-interface allows the radiologist to record any number of additional 2D and 3D images as secondary attributes of a diagnostic finding. For example, a "colon:polyp" diagnostic finding could be supported by additional 3D snapshots of the polyp. In the case of "spine:arthritis" which is seen over a large portion of the skeleton, a single diagnostic finding can be created to establish the diagnosis, and additional snapshots of other sites of the disease can support the diagnosis. Alternatively, creating multiple individual diagnostic findings documenting arthritis could achieve the same result. Additionally, the recording system provides the ability to place a marking symbol in the 2D or 3D images indicating the location of the selected feature. The snapshot function also records the location of the marking symbol visible within the 2D or 3D viewer, as well as the state of the 2D or 3D viewer at which time the Sn button was pressed.

A movie button, Mo, functions in a similar manner by appending cine clips of moving 2D or 3D images, including active annotations and voice descriptions. The active annotations can take the form of freehand notations "drawn" over the 2D or 3D images during recording of the cine clip. The drawn freehand notations can be similar to "chalkboard-style" markings used by television commentators to diagram and analyze football plays.

To assist radiologists in establishing a diagnosis, the annotation menus may also provide links to reference materials and example images related to each potential diagnostic finding. The annotation menus may include options to undo accidental RMB clicks. The reporting system 10 also permits the radiologist to recall the annotation menus to reassign a diagnostic code to a particular finding if the diagnosis is revised during the evaluation process.

The reporting system 10 may also perform computerized diagnoses at step 320. For example, computer-assisted polyp detection (CAPD), as disclosed in U.S. Pat. No. 5,920,319, can be integrated with the system so that CAPD-identified polyps can be automatically correlated with radiologist-defined polyps by correlating the proximity (i.e., Euclidean distances) of image finding coordinates. The identified diagnostic findings can be used to support advanced applications, such as the creation of "polyp maps" for subsequent endoscopic or surgical guidance. A polyp map consists of a 3D-rendered colon with highlighted polyp locations.

Another example of an advanced application that this reporting system supports is a Transbronchial Needle Aspiration (TBNA) targeting scheme. The TBNA application uses the stored data in the reporting system 10 to automatically construct airway models and lymph node targets (i.e., surface-rendered models of the anatomy generated using the respective finding coordinates). TBNA is a bronchoscopy technique that permits a needle biopsy of suspicious mediastinal lymph nodes. The tracheobronchial tree and lymph nodes are defined by their diagnostic finding coordinates, respectively, and are assigned secondary attributes by the radiologist to indicate the TBNA lymph nodes as targets. Further refinement of the lymph node targets (i.e., modeling lymph nodes as spherical or ellipsoid objects) can use the distance, area, and volume measurements that are generated as secondary attributes of those lymph nodes.

After the review of the image(s) is deemed complete, the report display is presented for the radiologist to review at step 332. The report display is invoked by pressing a report button in the user-interface to activate the report display. Alternately, when using a two-monitor system or a wide monitor display, the report can be shown simultaneously as it is being generated. The reporting system 10 sorts the diagnostic findings according to anatomical categories, with high priority findings placed at the top of each category. The reporting system 10 can also order the findings by priority levels, irrespective of anatomical categories. The reporting system 10 highlights each high-priority finding with color-enhanced text. The radiologist edits the final report as necessary, including linking redundant findings at step 324.

A powerful feature of the paradigm's report format and database structure is the ability to link and track diagnostic findings within the same examination (i.e., vertical linking) and across serial examinations (i.e., horizontal linking). For example, a CT examination generally consists of a hierarchy of series/acquisitions/images. A diagnostic finding identified on an image within one series may also be seen in another series of the same examination. The reporting system 10 provides the ability to vertically link (i.e., combine) such diagnostic findings within its database. In one implementation, the radiologist "drags and drops" a finding onto a matching finding in the report display to achieve linking, and the "dropped" finding becomes a subset of the primary finding. Alternatively, the reporting system 10 could perform linking via a command-line interface or voice-activated control. The purpose of vertical linking is to manage redundancy of report information.

Similarly, the reporting system 10 provides horizontal linking as a means to track and monitor a diagnostic finding over time and across various imaging modalities. In horizontal linking, diagnostic findings can be "dragged and dropped" across new paradigm reports. In this case, the diagnostic findings exist independently in their respective reports and do not necessarily become subsets of other findings. Horizontal linking provides a means to efficiently analyze a particular diagnostic finding over time.

An extension of "linking" is "compositing." A group of image findings (e.g., pleura:pleural effusion, heart:cardiomegaly, lung:pulmonary edema) can be linked (or composited) by the radiologist or by an artificial intelligence (AI) program to yield a cumulative diagnosis of "congestive heart failure." Similarly, the radiologist or an AI program can link or composite other clinical information (e.g., laboratory values or pathology reports) to support and make a diagnosis.

The reporting system 10 also allows for the automatic incorporation of repetitive findings from previous reports into a new report (e.g., evidence of prior gallbladder surgery). If a previous report contains a "trackable" finding (e.g., index lymph node measurement), that previous finding is brought to the attention of the radiologist. In this case, the trackable finding can be linked horizontally across reports, and the temporal progression of this finding can be observed in a specialized viewer.

The report display also includes a suspend-resume button for suspending or resuming an examination in case the radiologist is interrupted during the review. Upon completion of the report, the reporting system 10 stores and sends the final report, as shown in FIGS. 7A–C, at step 326. The reporting system 10 may issue the report by any combination of telephone, fax, pager, or e-mail and may include return receipt verification. The automated sending and receipt verification allows the radiologist to quickly communicate his or her findings and track this communication. Along with the prioritized and highlighted presentation of the most significant findings, the automated sending feature of the reporting system 10 helps to fulfill the radiologist's duty for timely communication of results and follow-up on the findings.

The reporting system also supports "real-time dynamic radiology." Each diagnostic finding is annotated with a timestamp. After an initial report is "signed off," any future changes to the report can be recorded as a history of the report. Any subsequent significant changes can be automatically communicated to a clinician and verified upon their receipt.

The reporting system 10 monitors how the radiologist reviews an examination. The final report can also indicate how much time a radiologist spends reviewing an exam, number of findings, and average time per finding. Statistics, including total review time, time per finding, number of findings, and diagnostic accuracy, are compiled during a review session and are reported as needed. This feature creates a utilization management and quality assurance measure that is appealing to the Health Care Financing Administration (HCFA) and health maintenance organizations (HMOs).

The final report can also be automatically translated into a foreign language using the standardized lexicon of anatomical:pathological codes and simple lookup tables.

Healthcare organizations further benefit from the automation and efficiency of the system. In particular, billing speed and accuracy are increased. Billing requires matching of ICD and CPT codes, a task that currently requires highly-trained personnel to decipher radiology reports and verify proper code assignments. Incorrect coding results in denied or delayed reimbursement by insurers. However, the present reporting system automate the process and allows radiologists to assume responsibility for coding.

Figure 4:
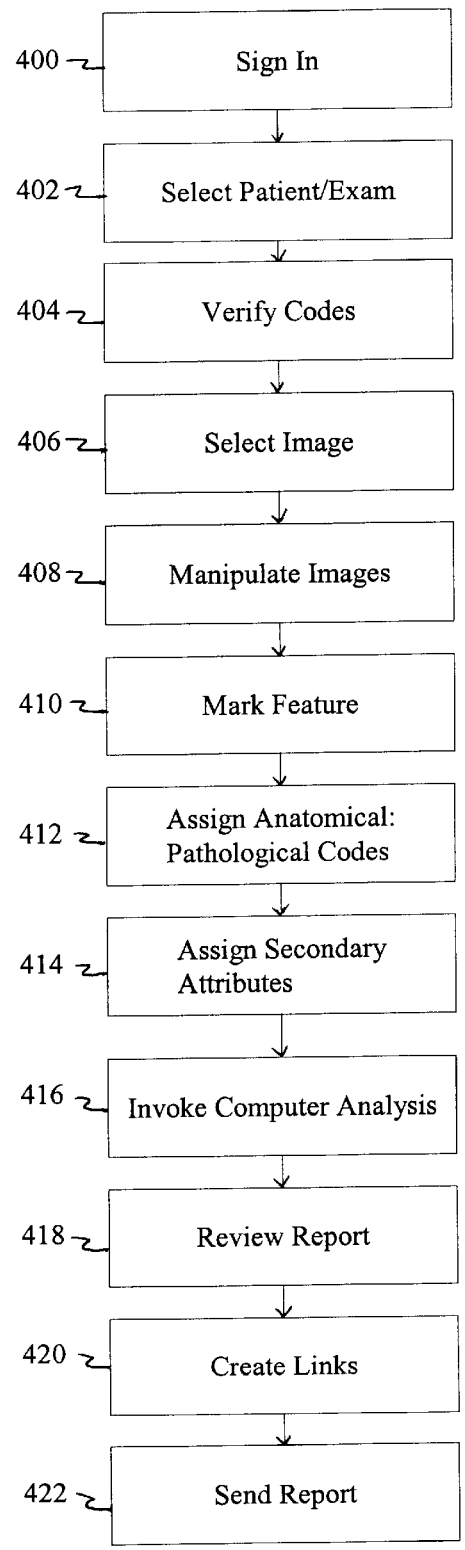
FIG. 4 illustrates a flowchart representing steps of operation of the method of the present invention.

The method of operation is best illustrated by its application in the field of radiology as shown in FIG. 4. Upon starting the software program, the radiologist signs in, with either a password or voice signature or any other security measure, to begin the evaluation at step 400. Secure sign-in protects access to the database and validates the identity of the radiologist generating the report. The file loader displays a work list of patients whose examination studies are accessible. The radiologist selects the name of a patient at step 402, and the file loader displays all of the associated unread examination files. The radiologist selects a particular examination file, and that examination file is loaded into computer memory.

The file loader displays the CPT and ICD codes assigned to a particular examination. This information can be obtained from the HIS 36 or entered manually. The radiologist verifies the CPT and ICD codes and makes any necessary changes at step 404. Correct assignment of the CPT and ICD codes by the radiologist is essential for electronic billing and expedited reimbursement by insurers.

After validation of the CPT and ICD codes, the radiologist begins analysis of the first image presented in the 2D viewer or selects an alternate image, at step 406, from the series menu which lists all of the images or sets of images (i.e., series) in a patient exam available for review. The radiologist may change the displayed image in order to locate diagnostically significant features in other images at step 408. For example, the radiologist may press the LMB while moving the mouse to pan through multiple images in the 2D viewer (provided that more than one image is contained in the series). The radiologist may also translate the displayed image up, down, and sideways by pressing the MMB while moving the mouse. The radiologist may also zoom the displayed image by pressing the LMB and MMB simultaneously while moving the mouse. In the 3D viewer, the mouse operations are similar except that pressing the LMB while moving the mouse causes the 3D rendered scene to rotate in space or to guide a "fly-through." Alternatively, multiple images or series can be displayed simultaneously in separate windows in the viewer.

To aid in the identification of diagnostically significant features, the radiologist may toggle between 2D and 3D viewers by pressing the 2D/3D toggle button as shown in FIG. 6. When the 3D viewer is initially activated, a volume-rendered image centered around the coordinates of the identified feature is created (i.e., a cube of CT data is volume-rendered). The radiologist may adjust the size of the volume (i.e., cube of digital data) that is rendered in the 3D viewer via the render-box-size menu. The radiologist may further adjust the volume-rendered image in various ways, such as using opacity maps, cut planes, and rotation. MPR and surface rendering can also be activated in the 3D viewer.

When the radiologist toggles between 2D and 3D viewers, the last state of each viewer is recalled. The radiologist may also toggle between the 3D and 2D viewers by clicking on a primary 2D thumbnail image representation of a diagnostic finding (or its supporting secondary 2D and 3D thumbnails), thereby recalling the last state of the 2D or 3D viewer associated with the activated finding. The cursor position and location of any marking symbols in the display are recalled as part of the last state of the viewer. The 2D or 3D viewer then enters an edit mode, during which the radiologist can append additional secondary attributes to the activated diagnostic finding, and these are subsequently stored in proper locations within the database.

The radiologist can also set the orientation of the image data prior to image analysis. If an image or image series needs to be reoriented, the radiologist pans through the volume of images to locate the most superior image (or close to it). Then, the radiologist toggles the orientation button, at which time the viewer goes into an orientation mode. The radiologist rotates the image plane by pressing the LMB and moving the mouse until the proper anterior/posterior and left/right orientation is achieved. Finally, the radiologist toggles the orientation button again to set the proper orientation. The viewer automatically adjusts the 2D image plane so that it is orthogonal to the radiologist's viewpoint.

The radiologist has further control over the display of the images such as grayscale (or color scale) and 3D opacity maps settings. The radiologist may toggle between the two most recent W/L settings or Op settings in the 2D and 3D viewers by pressing the previous button, Pr, as shown in FIG. 6, or simultaneously pressing the LMB and RMB. Additionally, the radiologist may toggle a visible cursor on and off by pressing a cursor-toggle button, Cr, as shown in FIG. 6, to indicate the location of a finding in both the 2D and 3D viewers. By pressing the overview button, the radiologist re-centers a 2D or 3D volume-rendered image in case the scene is moved out of sight.

When the radiologist locates a diagnostically significant feature, the radiologist, positions the cursor over the location of the feature on the digital image and clicks the RMB to mark the feature at step 410. Clicking on the RMB stores the image coordinates and image number corresponding to the cursor location in database. To complete the definition of a diagnostic finding, the radiologist annotates the point (location) by assigning an anatomical:pathological code and optionally assigning secondary attributes at steps 412 and 414.

The radiologist selects an anatomical:pathological code from a predefined lexicon, such as the ACR Index of Radiological Diagnoses or SNOMED or a custom designed lexicon, to create a diagnostic finding. As each diagnostic finding is created, a representative thumbnail image 620 may be displayed on the right side of the 2D and 3D viewers, or in a separate display, for immediate review and recall, and the thumbnail images later may be incorporated into the final report as shown in FIGS. 7B and 7C.

Figure 5A:
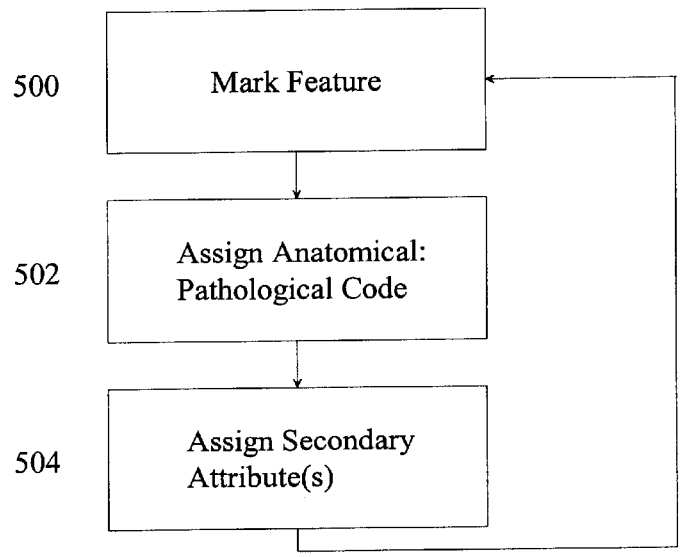
FIGS. 5A and 5B illustrate the steps of annotating findings.

The radiologist enters the anatomical:pathological code by one of several modes. In a first mode, "click and label", cascading pop-up annotation menus are presented to the radiologist immediately after a feature is marked by an RMB click at step 500 of FIG. 5A. The radiologist selects an appropriate anatomical location description from the anatomical-location menu at step 502. For example, the radiologist may select Gastrointestinal System: Colon: Sigmoidal Colon. After the selection, the radiologist selects the pathological description from the pathology-description menu at step 502. For example, the radiologist may select Neoplasm:Benign Neoplasm:Polyp. A secondary attribute may then be assigned at step 504.

Figure 5B:
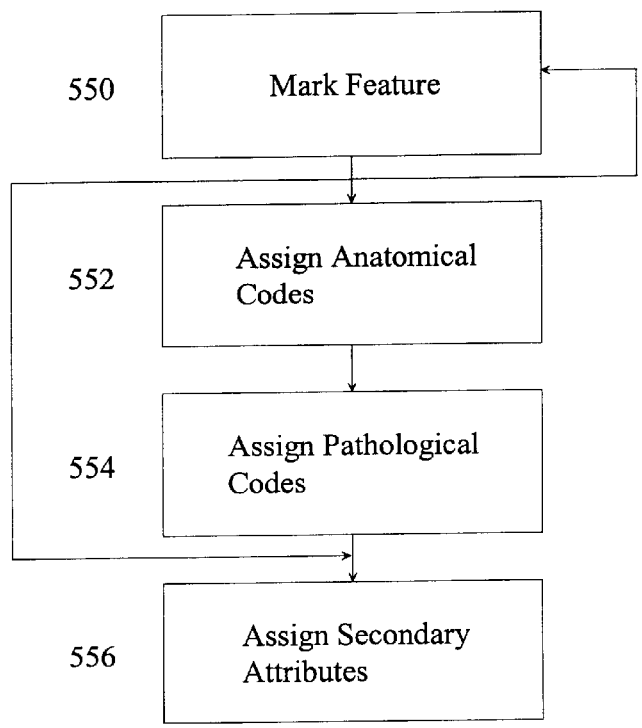

In a second mode, "click-click-click and label-label-label", the radiologist identifies all the diagnostically significant features first and subsequently annotates the features with labels and secondary attributes. As shown in FIG. 5B, the radiologist marks a designated feature at step 550 and then proceeds to mark successive features by repeating step 550. After all desired features are marked, the radiologist assigns a diagnostic code to each marked feature by assigning an anatomical code at step 552 and a pathological code at step 554. Secondary attributes are assigned at step 556 either following the marking of a feature at step 550 or the assigning of anatomical and pathological codes at steps 552 and 554. The radiologist must assign a diagnostic code to any unlabeled findings prior to final report approval; otherwise, these findings may be labeled with a default "unknown location:unknown pathology." Additionally, the radiologist may recall the annotation menus to reassign an anatomical:pathological code to a particular finding if the diagnosis needs to be revised during the evaluation process.

The radiologist may also assign secondary attributes to embellish or support a diagnostic finding at step 414, but secondary attributes are not essential for establishing a diagnostic finding. The radiologist may enter descriptive characteristics, dimensional measurements, audio descriptions, and specific snapshots of particular views of the identified finding as secondary attributes. For example, the radiologist may add descriptive characteristics that enhance a specific diagnostic code set from a characteristics menu of descriptive characteristics.

The radiologist may measure one or more dimensions of a finding, for example, a diameter of an identified feature in the 2D or 3D image. The radiologist activates the distance measuring function by pressing the distance-measurement button, Di, as shown in FIG. 6. The radiologist measures the distance by clicking on first and second object points which span the characteristic length. Similarly, the radiologist may measure the area of an identified feature by pressing the area-measurement button, Ar, as shown in FIG. 6 and defining a region-of-interest (ROI) using the input device 27. The cross-sectional area, mean voxel value, and standard deviation of voxel values in the ROI can be calculated. The radiologist may also add a volume-measurement as a secondary attribute by pressing the volume-measurement button, Vo, as shown in FIG. 6.

As part of step 414, the radiologist may also add a priority level and recommendation to the diagnostic finding by pressing the priority button, Pt, or recommendation button, Rm, respectively, as shown in FIG. 6. In addition, the radiologist may append a verbal description of the diagnostic finding in the form of an audio file. To add a verbal description the radiologist presses the audio button, Au, as shown in FIG. 6 to initiate recording and then dictates a verbal description of the diagnostic finding. The radiologist presses the audio button again to stop recording, and an audio file of the verbal description is stored in the database attached to the finding. Audio files can be attached to the "global" finding or attached to individual snapshot images or movies.

Additionally, the radiologist may record snapshots of any of the displayed 2D and 3D images as a secondary attribute by pressing the snapshot button, Sn, as shown in FIG. 6. For example, the radiologist may record any number of additional images showing differing views of a particular diagnostically significant feature. For example, a "colon:polyp" diagnostic finding could be supported by additional 3D snapshots of the polyp. The radiologist may also append cine clips of moving 2D or 3D images (including audio and active annotations) as a secondary attributes in a manner similar to recording snapshots by pressing the movie button, Mo, as shown in FIG. 6. Pressing of the movie button starts and stops the recording of the cine clip.

Prior to final report review, the radiologist may also invoke computer-aided location and analysis of diagnostically significant features, at step 416, whereby the system automatically identifies and diagnoses suspicious features. For example, the radiologist can review polyps found by the CAPD that were not previously identified by the radiologist.

After the radiologist's review is deemed complete, the radiologist clicks a report button on the bottom of either the 2D or 3D viewer as shown in FIGS. 6 to activate the report display at step 418. Alternately, the report can be generated and simultaneously displayed on a second monitor while the diagnostically significant findings are being located and coded. The diagnostic findings are sorted according to anatomical categories and priorities, with high priority findings being placed at the top of each category. Each high-priority finding is highlighted with color-enhanced text. The sorting and highlighting of the diagnostic findings alerts the end-user to the most significant diagnostic findings.

The radiologist edits the final report as necessary, including linking redundant findings at step 420. The step of creating links, step 420, may be performed before or after the step of reviewing the report, step 418, as depicted in FIG. 1, where the step of creating the links, step 110, occurs prior to the step of reviewing the report, step 112. In one implementation of vertical linking, the radiologist "drags and drops" a finding onto a matching finding in the same report display, and the "dropped" finding becomes a subset of the primary finding. Alternatively, the radiologist can form links via a command-line interface or voice-activated commands (control). Similarly, the radiologist may assign horizontal linking to track and monitor a diagnostic finding over time and across various imaging modalities. In horizontal linking, diagnostic findings can be "dragged and dropped" across new paradigm reports in a similar fashion.

The radiologist may also composite a group of image findings to yield a diagnosis as illustrated above for "congestive heart failure." In this process, the radiologist or an AI program can link (or composite) additional clinical information (e.g., laboratory and pathology report values) to support a diagnosis.

The radiologist further reviews any repetitive diagnostic findings from previous reports which are brought to the attention of the radiologist by the system. If a previous report contains a repetitive diagnostic finding (e.g., evidence of prior gallbladder surgery), that finding is presented to the radiologist for automatic incorporation into the new report. If a previous report contains a "trackable" diagnostic finding (e.g., index lymph node measurement), the radiologist can link the trackable diagnostic findings horizontally across reports, and the temporal progression of this diagnostic finding can be observed in a specialized viewer.

The radiologist can suspend an examination for later resumption by pressing the suspend-resume button during the review. Upon completion of the report the radiologist instructs the system to send the report to the end-users (e.g., clinicians) at step 422. Additionally, the end-user can access the report via a Web server after the report has been posted. As noted above, the report may be sent by a combination of telephone, fax, pager, or e-mail and may include return receipt verification. The automated sending and receipt verification allows the radiologist to quickly communicate his or her findings and verify this communication.

End-users receiving the radiologist's report can customize the display of the information to best suit their needs. For example, the clinician can click on a thumbnail image in the final report to access the original PACS image data. Additionally, the reporting system can automatically translate the radiologist's report into a different language for the end-user. The standardized lexicon of diagnostic findings supports rapid translation of reports to foreign languages by employing translation look-up tables.

The reporting system of the present invention has further application beyond the preparation and delivery of reports. The ability of the reporting system to enter diagnostic findings into searchable databases readily supports data mining for clinical trials, epidemiology studies, and outcomes analyses.

Additionally, the reporting paradigm supports radiologic training. For example, a radiology resident can issue a preliminary report indicating his or her findings, and the preliminary report can later be modified by an attending radiologist to indicate any corrections. In the latter case, the system automatically informs the referring clinician of any significant changes. The history of report changes can be recorded with each finding (or changed finding) having a timestamp. The reporting scheme also supports standardized testing (e.g., replacement of the American Board of Radiology's Oral Board examination) by objectively measuring a student's performance. Such an objective performance measure could also assist in comparing a radiologist's performance to that of a non-radiologist.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. For example, while the above invention has been illustrated in terms of its application to the field of radiology, the invention is equally applicable to other fields of medicine as well as other image analysis fields such as satellite imagery and photography. It should therefore be understood that this invention is not limited to the particular embodiments described herein, but is intended to include all changes and modifications that are within the scope and spirit of the invention as set forth in the claims.

What is claimed is:

1. A computer implemented method for analysis of an image comprising the steps of:
   displaying an actual image of an object in an image viewer to a user for analysis of the image;
   associating image content information describing the image type with the image;
   analyzing the image to identify a feature of interest of the object;
   identifying a location of the feature using an input device to selectively mark a location on the actual image representing image coordinates of the identified feature;
   associating a position descriptor with the location of the feature, the position descriptor representing image coordinates;
   compiling a list of user-selectable items related to the image content information to present to the user;
   selecting at least one item from the list, the item describing a characteristic of the feature; and
   creating an image finding of the feature comprising the position descriptor and the at least one selected item.

2. A method according to claim 1 comprising associating a status of the viewer with the feature, the status comprising at least one of an orientation, a magnification, and a shading of the image, and wherein the image finding comprises the viewer status.

3. A method according to claim 1 wherein the at least one list item comprises a location-code which describes the location of the feature relative to an object depicted in the image.

4. A method according to claim 3 wherein the location-code represents an anatomical location.

5. A method according to claim 1 wherein the image content information comprises one or more of a CPT code and a ICD code.

6. A method according to claim 3 wherein the location-code is selected from a predefined lexicon of location-codes.

7. A method according to claim 3 wherein the at least one list item comprises a description-code which describes at least one property of the feature.

8. A method according to claim 7 wherein the description-code is selected from a predefined lexicon of description-codes.

9. A method according to claim 1 comprising associating at least one of a dimensional measurement, mean voxel value, standard deviation of voxel values, an audio description, a two-dimensional image, a three-dimensional rendered image, a video description, and a user-defined illustration with the finding.

10. A method according to claim 1, wherein the image content information denotes that at least one specific object is depicted within the image.

11. A method according to claim 7 wherein the property includes a pathology of the feature.

12. A method according to claim 1 wherein the selected item is entered using voice recognition.

13. A method according to claim 1 comprising the step of assigning a priority to the image finding to denote the importance of the image finding.

14. A method according to claim 1 comprising the step of assigning a recommendation to the image finding to denote a recommended action to be taken with respect to the image finding.

15. A method according to claim 1 comprising the steps of creating at least one thumbnail image of the feature and associating the thumbnail image with the image finding.

16. A method according to claim 15 comprising the step of displaying the thumbnail image.

17. A method according to claim 1 comprising the step of displaying the image in at least one of a two-dimensional viewer and a three-dimensional viewer.

18. A method according to claim 17 wherein the image is formed by at least one of volume rendering, surface rendering, and rendering about a point.

19. A method according to claim 17 comprising the step of displaying multiple images simultaneously.

20. A method according to claim 1 wherein the image includes a digital image.

21. A method according to claim 1 wherein the image is part of a series of two-dimensional images associated with a three-dimensional body.

22. A method according to claim 1 comprising the step of identifying features in the image using computer analysis of the image to provide computer identified features.

23. A method according to claim 22 comprising the step of correlating the computer identified features with the feature.

24. A method according to claim 22 wherein the computer analysis includes computer assisted polyp detection.

25. A method according to claim 22 wherein the computer analysis includes a transbronchial needle aspiration targeting scheme.

26. A method according to claim 1 comprising creating a plurality of image findings.

27. A method according to claim 26 comprising the step of linking selected findings of the plurality of image findings to create a cumulative finding encompassing the plurality of image findings.

28. A method according to claim 26 comprising the step of linking related findings to associate the related findings to render the associated findings retrievable as a unit.

29. A method according to claim 26 comprising the steps of assigning a priority to at least one of the image findings and sorting the image findings according to priority.

30. A method according to claim 26 comprising the steps of assigning a location-code to at least one of the image findings and sorting the image findings according to location-code.

31. A method according to claim 26 comprising the step of assigning a description-code to at least one of the image findings and sorting the image findings according to the description-code.

32. A method according to claim 1 comprising the steps of
retrieving at least one prior finding from a previous analysis of an image and
linking the retrieved image finding to the image finding of the feature, whereby a set of findings is created describing a chronology of the image finding of the set feature.

33. A method according to claim 1 comprising the step of generating a report based on the image finding.

34. A method according to claim 1 comprising the step of recording a cine clip showing a time varying characteristic of the feature.

35. A method according to claim 33 wherein the report contains at least one of the image finding, a thumbnail image of an image finding, and a chronology of an image finding.

36. A computer implemented method for analysis of image data comprising the steps of:
displaying an actual image of an object in an image viewer to a user for analysis of the image;
analyzing the image to identify a feature of interest of the object;
identifying a location of the feature using an input device to selectively mark a location on the actual image representing image coordinates of the identified feature;
associating a status of the viewer with the feature, the status comprising at least one of an orientation, a magnification, and a shading of the image;
associating a position descriptor with the location of the feature, the position descriptor representing image coordinates;
associating a location-code with the feature, the location-code selected from a list presented to the user and describing the location of the feature relative to the object;
associating a description-code with the feature to describe a characteristic of the feature, the description-code selected from a list presented to the user; and
creating an image finding of the feature comprising the position descriptor, the location-code, the viewer status, and the description-code.

37. A method according to claim 36 wherein the location-code represents an anatomical location.

38. A method according to claim 36 wherein the list of location-codes is compiled from a predefined lexicon of location-codes.

39. A method according to claim 36 wherein the characteristic describes at least one physical property of the feature.

40. A method according to claim 36 wherein the list of description-codes is compiled from a predefined lexicon of description-codes.

41. A method according to claim 36 comprising the step of associating a content-code with the image, the content-code denoting that at least one specific object is depicted within the image, and wherein the description-code list is assembled to contain description-codes that are consistent with the content-code.

42. A method according to claim 38 comprising the step of associating a content-code with the image, the content-code denoting that at least one specific object is depicted within the image and wherein the location-code list is assembled to contain location-codes that are consistent with the content-code.

43. A method according to claim 36 wherein the characteristic includes a pathology of the feature.

44. A method according to claim 36 comprising associating at least one of a dimensional measurement, mean voxel value, standard deviation of voxel values, an audio description, a two-dimensional image, a three-dimensional rendered image, a video description, and a user-defined illustration with the finding.

45. A method according to claim 36 comprising the step of creating at least one thumbnail image of the feature and associating the thumbnail image with the image finding.

46. A method according to claim 45 comprising the step of displaying the thumbnail image wherein selection of the thumbnail image recalls the associated image finding.

47. A method according to claim 36 comprising the step of displaying the image includes display in at least one of a two-dimensional viewer and a three-dimensional viewer.

48. A method according to claim 47 wherein the image is formed by at least one of volume rendering, surface rendering, and rendering about a point.

49. A method according to claim 47 comprising the step of displaying multiple images simultaneously.

50. A method according to claim 36 wherein the image data includes a digital image.

51. A method according to claim 36 wherein the image data includes a series of two-dimensional images associated with a three-dimensional body.

52. A method according to claim 36 comprising the step of identifying features in the image using computer analysis of the image to provide computer identified features.

53. A method according to claim 52 comprising the step of correlating the computer identified features with the feature.

54. A method according to claim 36 comprising creating a plurality of image findings.

55. A method according to claim 54 comprising the step of generating a report based on the image findings.

56. A method according to claim 36 comprising the step of recording a cine clip showing a time varying characteristic of the feature.

57. A method according to claim 55 wherein the step of generating the report comprises incorporating a cumulative finding by linking selected findings of the plurality of image findings to create the cumulative finding encompassing the plurality of image findings.

58. A method according to claim 55 wherein the step of generating the report comprises incorporating a primary finding by linking related findings to associate the related findings to create the primary finding.

59. A method according to claim 55 wherein the step of generating the report comprises the step of assigning a priority to at least one of the image findings and sorting image findings according to priority.

60. A method according to claim 55 wherein the step of generating the report comprises the step of sorting image findings according to at least one of the location-code and the description-code.

61. A method according to claim 55 wherein the step of generating the report comprises incorporating a chronology of an image finding by
retrieving at least one previous finding associated with the feature from a previous analysis and
linking the retrieved image finding to the image finding of the feature whereby the chronology of the image finding of the feature is created.

62. A method according to claim 1 including the steps of displaying a selected portion of the image and selecting of the displayed portion of the image to recall the associated diagnostic finding.

63. A method according to claim 1 wherein the image includes a plurality of views having differing perspectives of the feature.

64. A method according to claim 55 wherein the step of generating the report comprises computing a selected statistical measure of the report generation process.

65. A method according to claim 64 wherein the statistical measure includes at least one of total review time, time per finding, number of findings, and diagnostic accuracy.

66. A method according to claim 55 comprising generating billing information to create a bill for the report.

67. A method according to claim 1 wherein the image content information includes an image content-code, denoting what the image data depicts, and includes reason-code, denoting a reason for creating the image data.

68. A method according to claim 67 comprising the step of ensuring that the image content-code and reason-code are compatible.

69. A method according to claim 1, wherein the list of user-selectable items is at least a subset of a comprehensive list of user selectable items.

70. A method according to claim 2, wherein the orientation comprises at least one of a translation state and a rotation state.

71. A method according to claim 2, wherein the magnification comprises a degree of image zoom.

72. A method according to claim 2, wherein the shading comprises at least one of a gray scale setting and opacity setting.

73. A method according to claim 36, wherein the orientation comprises at least one of a translation state and a rotation state.

74. A method according to claim 36, wherein the magnification comprises a degree of image zoom.

75. A method according to claim 36, wherein the shading comprises at least one of a gray scale setting and opacity setting.

76. A system for analyzing an image, comprising:
a display for displaying an actual image of an object in an image viewer to a user for analysis of the image;
a content information retriever for retrieving image content information describing the image type and for associating the content information with the image;
an input device for marking a location on the actual image representing image coordinates of an image feature;
a list compiler for compiling a list of user-selectable items related to the image content information and for presentation the list to the user; and
an image finding generator for creating an image finding of the feature comprising the image coordinates of the image feature and at least one item selected by the user from the list.

77. A system according to claim 76, comprising a viewer status recorder for associating a status of the viewer with the feature, the status comprising at least one of an orientation, a magnification, and a shading of the image.

78. A system according to claim 77, wherein the orientation comprises at least one of a translation state and a rotation state.

79. A system according to claim 77, wherein the magnification comprises a degree of image zoom.

80. A system according to claim 77, wherein the shading comprises at least one of a gray scale setting and opacity setting.

81. A system according to claim 76, wherein the list items comprise a location-code which describes the location of the feature relative to an object depicted in the image.

82. A system according to claim 81, wherein the location-code represents an anatomical location.

83. A system according to claim 81, wherein the location-code is selected from a predefined lexicon of location-codes.

84. A system according to claim 81, comprising a finding sorter for sorting a plurality of image findings according to location-code.

85. A system according to claim 76, wherein the list items comprise a description-code which describes at least one property of the feature.

86. A system according to claim 85, comprising a finding sorter for sorting a plurality of image findings according to description-code.

87. A system according to claim 85, wherein the description-code is selected from a predefined lexicon of description-codes.

88. A system according to claim 85, wherein the property includes a pathology of the feature.

89. A system according to claim 76, wherein the image content information comprises one or more of a CPT code and a ICD code.

90. A system according to claim 76, comprising a finding annotator for associating at least one of a dimensional measurement, mean voxel value, standard deviation of voxel values, an audio description, a two-dimensional image, a three-dimensional rendered image, a video description, and a user-defined illustration with the finding.

91. A system according to claim 76, comprising a voice recognition unit for entering the selected item.

92. A system according to claim 76, wherein the finding generator is configured to associate a priority with the image finding to denote the importance of the image finding.

93. A system according to claim 92, wherein the finding generator is configured to sort the image findings according to priority.

94. A system according to claim 76, wherein the finding generator is configured to associate a recommendation with the image finding to denote a recommended action to be taken with respect to the image finding.

95. A system according to claim 76, comprising a thumbnail generator for creating at least one thumbnail image of the feature and associating the thumbnail image with the image finding.

96. A system according to claim 76, wherein the viewer comprises at least one of a two-dimensional viewer and a three-dimensional viewer.

97. A system according to claim 76, comprising a renderer for generating the image by at least one of volume rendering, surface rendering, and rendering about a point.

98. A system according to claim 76, comprising an image analyzer for identifying features in the image using computer analysis of the image to provide computer identified features.

99. A system according to claim 98, wherein the image analyzer is configured to correlate the computer identified features with the feature.

100. A system according to claim 94, wherein the image analyzer is configured to perform computer assisted polyp detection.

101. A system according to claim 94, wherein the image analyzer is configured to perform a transbronchial needle aspiration targeting scheme.

102. A system according to claim 76, comprising a finding compositor for linking selected findings of a plurality of image findings to create a cumulative finding comprising the plurality of image findings.

103. A system according to claim 76, comprising a file loader for retrieving at least one prior finding from a previous analysis of an image and for linking the retrieved image finding to the image finding of the feature, whereby a set of findings is created describing a chronology of the image finding of the feature.

104. A system according to claim 76, comprising a report generator for generating a report based on the image finding.

105. A system according to claim 104, wherein the report contains at least one of the image finding, a thumbnail image of the image finding, and a chronology of the image finding.

106. A system according to claim 76, wherein the list of user-selectable items is at least a subset of a comprehensive list of user selectable items.

107. A system according to claim 76, comprising a communication interface for communication with at least one of the Internet, an e-mail system, a fax, a telephone, a wireless communications system, a pager, a cell phone, a hospital information system, a radiology information system, and a picture archiving and communication system.

108. A system for analyzing an image, comprising:
  display means for displaying an actual image of an object in an image viewer to a user for analysis of the image;
  content information retrieval means for retrieving image content information describing the image type and for associating the content information with the image;
  input means for marking a location on the actual image representing image coordinates of an image feature;
  list compilation means for compiling a list of user-selectable items related to the image content information for presentation to the user; and
  finding creation means for creating an image finding of the feature comprising the image coordinates of the image feature and at least one item selected by the user from the list.

109. A system according to claim 108, comprising a viewer status association means for associating a status of the viewer with the feature, the status comprising at least one of an orientation, a magnification, and a shading of the image.

110. A system according to claim 109, wherein the orientation comprises at least one of a translation state and a rotation state.

111. A system according to claim 109, wherein the magnification comprises a degree of image zoom.

112. A system according to claim 109, wherein the shading comprises at least one of a gray scale setting and opacity setting.

113. A system according to claim 108, wherein the list items comprise a location-code which describes the location of the feature relative to an object depicted in the image.

114. A system according to claim 113, wherein the location-code represents an anatomical location.

115. A system according to claim 113, wherein the location-code is selected from a predefined lexicon of location-codes.

116. A system according to claim 113, comprising a sorting means for sorting a plurality of image findings according to location-code.

117. A system according to claim 108, wherein the list items comprise description-codes which describes at least one property of the feature.

118. A system according to claim 117, comprising a sorting means for sorting a plurality of image findings according to description-code.

119. A system according to claim 117, wherein the description-code is selected from a predefined lexicon of description-codes.

120. A system according to claim 117, wherein the property includes a pathology of the feature.

121. A system according to claim 108, wherein the image content information comprises one or more of a CPT code and a ICD code.

122. A system according to claim 108, an annotation association means for associating at least one of a dimensional measurement, mean voxel value, standard deviation of voxel values, an audio description, a two-dimensional image, a three-dimensional rendered image, a video description, and a user-defined illustration with the finding.

123. A system according to claim 108, comprising a voice recognition unit for entering the selected item.

124. A system according to claim 108, wherein the finding creation means is configured to associate a priority with the image finding to denote the importance of the image finding.

125. A system according to claim 124, wherein the finding creation means is configured to sort the image findings according to priority.

126. A system according to claim 108, wherein the finding creation means is configured to associate a recommendation with the image finding to denote a recommended action to be taken with respect to the image finding.

127. A system according to claim 108, comprising a thumbnail creation means for creating at least one thumbnail image of the feature and associating the thumbnail image with the image finding.

128. A system according to claim 108, wherein the viewer comprises at least one of a two-dimensional viewer and a three-dimensional viewer.

129. A system according to claim 108, comprising a rendering means for rendering the image by at least one of volume rendering, surface rendering, and rendering about a point.

130. A system according to claim 108, comprising an image analysis means for analyzing the image to identify features in the image using computer analysis of the image to provide computer identified features.

131. A system according to claim 130, wherein the image analysis means is configured to correlate the computer identified features with the feature.

132. A system according to claim 130, wherein the image analysis means is configured to perform computer assisted polyp detection.

133. A system according to claim 130, wherein the image analysis means is configured to perform a transbronchial needle aspiration targeting scheme.

134. A system according to claim 108, comprising a finding linking means for linking selected findings of a plurality of image findings to create a cumulative finding comprising the plurality of image findings.

135. A system according to claim 108, comprising a file retrieval means for retrieving at least one prior finding from a previous analysis of an image and for linking the retrieved image finding to the image finding of the feature, whereby a set of findings is created describing a chronology of the image finding of the feature.

136. A system according to claim 108, comprising a report creation means for generating a report based on the image finding.

137. A system according to claim 136, wherein the report contains at least one of the image finding, a thumbnail image of the image finding, and a chronology of the image finding.

138. A system according to claim 108, wherein the list of user-selectable items is at least a subset of a comprehensive list of user selectable items.

139. A system according to claim 108, comprising a communication means for communication with at least one of the Internet, an e-mail system, a fax, a telephone, a wireless communications system, a pager, a cell phone, a hospital information system, a radiology information system, and a picture archiving and communication system.

140. A system for analyzing an image, comprising:
a display for displaying an actual image of an object in an image viewer to a user for analysis of the image;
an input device for marking a location on the actual image representing image coordinates of an image feature;
a viewer status recorder for associating a status of the viewer with the feature, the status comprising at least one of an orientation, a magnification, and a shading of the image;
a location-code list compiler for compiling a list of user-selectable location-codes describing the location of the feature relative to the object;
a description-code list compiler for compiling a list of user-selectable description-codes describing a characteristic of the feature; and
an image finding generator for creating an image finding of the feature comprising the image coordinates of the image feature, the viewer status, at least one location-code selected by the user from the location-code list, and at least one description-code selected by the user from the description-code list.

141. A system according to claim 140, wherein the location-code represents an anatomical location.

142. A system according to claim 140, wherein the list of location-codes is compiled from a predefined lexicon of location-codes.

143. A system according to claim 140, wherein at least one of the location-code list and the description-code list is at least a subset of a comprehensive list of user selectable items.

144. A system according to claim 140, comprising a content-code retriever for retrieving a content-code, denoting what the image data depicts, and for retrieving a reason-code, denoting a reason for creating the image data.

145. A system according to claim 140 wherein the characteristic describes at least one physical property of the feature.

146. A system according to claim 140, wherein the characteristic includes a pathology of the feature.

147. A system according to claim 140, wherein the list of description-codes is compiled from a predefined lexicon of description-codes.

148. A system according to claim 140, comprising a content-code retriever for retrieving a content-code and associating the content-code with the image, the content-code denoting that at least one specific object is depicted within the image, and wherein the location-code list is assembled to contain location-codes that are consistent with the content-code.

149. A system according to claim 140, comprising a content-code retriever for retrieving a content-code and associating the content-code with the image, the content-code denoting that at least one specific object is depicted within the image, and wherein the description-code list is assembled to contain description-codes that are consistent with the content-code.

150. A system according to claim 140, comprising a finding annotator for associating at least one of a dimensional measurement, mean voxel value, standard deviation of voxel values, an audio description, a two-dimensional image, a three-dimensional rendered image, a video description, and a user-defined illustration with the finding.

151. A system according to claim 140, comprising a thumbnail generator for creating at least one thumbnail image of the feature and associating the thumbnail image with the image finding.

152. A system according to claim 140, wherein the viewer comprises at least one of a two-dimensional viewer and a three-dimensional viewer.

153. A system according to claim 152, comprising a rendering means for rendering the image by at least one of volume rendering, surface rendering, and rendering about a point.

154. A system according to claim 140, comprising an image analyzer for identifying features in the image using computer analysis of the image to provide computer identified features.

155. A system according to claim 154, wherein the image analyzer is configured to correlate the computer identified features with the feature.

156. A system according to claim 140, comprising a report generator for generating a report based on the image finding.

157. A system according to claim 156, comprising a finding linking means for linking selected findings of a plurality of image findings to create a cumulative finding comprising the plurality of image findings.

158. A system according to claim 156, wherein the report generator is configured to assign a priority to at least one of a plurality of image findings and to sort the image findings according to priority.

159. A system according to claim 156, wherein the report generator is configured to sort image findings according to at least one of the location-code and the description-code.

160. A system according to claim 156, comprising a file loader for retrieving at least one prior finding from a previous analysis of an image and for linking the retrieved image finding to the image finding of the feature, whereby a set of findings is created describing a chronology of the image finding of the feature.

161. A system according to claim 156, wherein the report generator is configured to compute a selected statistical measure of the report generation process.

162. A system according to claim 161, wherein the statistical measure includes at least one of total review time, time per finding, number of findings, and diagnostic accuracy.

163. A system according to claim 140, comprising a bill generator for creating a bill based on the diagnostic finding.

164. A system according to claim 140, wherein the finding generator is configured to associate a recommendation with the image finding to denote a recommended action to be taken with respect to the image finding.

165. A system according to claim 140, wherein the orientation comprises at least one of a translation state and a rotation state.

166. A system according to claim 140, wherein the magnification comprises a degree of image zoom.

167. A system according to claim 140, wherein the shading comprises at least one of a gray scale setting and opacity setting.

168. A system for analyzing an image, comprising:

display means for displaying an actual image of an object in an image viewer to a user for analysis of the image;

input means for marking a location on the actual image representing image coordinates of an image feature;

viewer status association means for associating a status of the viewer with the feature, the status comprising at least one of an orientation, a magnification, and a shading of the image;

location-code list compilation means for compiling a list of user-selectable location-codes describing the location of the feature relative to the object;

description-code compilation means for compiling a list of user-selectable description-codes describing a characteristic of the feature; and finding creation means for creating an image finding of the feature, comprising the image coordinates of the image feature, the viewer status, at least one location-code selected by the user from the location-code list, and at least one description-code selected by the user from the description-code list.

169. A system according to claim 168, wherein the orientation comprises at least one of a translation state and a rotation state.

170. A system according to claim 168, wherein the magnification comprises a degree of image zoom.

171. A system according to claim 168, wherein the shading comprises at least one of a gray scale setting and opacity setting.

172. A system according to claim 168, wherein the location-code represents an anatomical location.

173. A system according to claim 168, wherein the list of location-codes is compiled from a predefined lexicon of location-codes.

174. A system according to claim 168, wherein at least one of the location-code list and the description-code list is at least a subset of a comprehensive list of user selectable items.

175. A system according to claim 168, comprising a content-code retriever for retrieving a content-code, denoting what the image data depicts, and for retrieving a reason-code, denoting a reason for creating the image data.

176. A system according to claim 168, wherein the characteristic describes at least one physical property of the feature.

177. A system according to claim 168, wherein the characteristic includes a pathology of the feature.

178. A system according to claim 168, wherein the list of description-codes is compiled from a predefined lexicon of description-codes.

179. A system according to claim 168, comprising a content-code retrieval means for retrieving a content-code and associating the content-code with the image, the content-code denoting that at least one specific object is depicted within the image, and wherein the location-code list is assembled to contain location-codes that are consistent with the content-code.

180. A system according to claim 168, comprising a content-code retrieval means for retrieving a content-code and associating the content-code with the image, the content-code denoting that at least one specific object is depicted within the image, and wherein the description-code list is assembled to contain description-codes that are consistent with the content-code.

181. A system according to claim 168, an annotation association means for associating at least one of a dimensional measurement, mean voxel value, standard deviation of voxel values, an audio description, a two-dimensional image, a three-dimensional rendered image, a video description, and a user-defined illustration with the finding.

182. A system according to claim 168, comprising a rendering means for rendering the image by at least one of volume rendering, surface rendering, and rendering about a point.

183. A system according to claim 168, comprising an image analyzer for identifying features in the image using computer analysis of the image to provide computer identified features.

184. A system according to claim 183, wherein the image analyzer is configured to correlate the computer identified features with the feature.

185. A system according to claim 168, comprising a report generator for generating a report based on the image finding.

186. A system according to claim 185, comprising a finding linking means for linking selected findings of a plurality of image findings to create a cumulative finding comprising the plurality of image findings.

187. A system according to claim 185, wherein the report generator is configured to assign a priority to at least one of a plurality of image findings and to sort the image findings according to priority.

188. A system according to claim 185, wherein the report generator is configured to sort image findings according to at least one of the location-code and the description-code.

189. A system according to claim 185, comprising a file loader for retrieving at least one prior finding from a previous analysis of an image and for linking the retrieved image finding to the image finding of the feature, whereby a set of findings is created describing a chronology of the image finding of the feature.

190. A system according to claim 185, wherein the report generator is configured to compute a selected statistical measure of the report generation process.

191. A system according to claim 190, wherein the statistical measure includes at least one of total review time, time per finding, number of findings, and diagnostic accuracy.

192. A system according to claim 168, comprising a bill generator for creating a bill based on the diagnostic finding.

193. A system according to claim 190, wherein the finding creation means is configured to associate a recommendation with the image finding to denote a recommended action to be taken with respect to the image finding.

* * * * *

UNITED STATES PATENT AND TRADEMARK OFFICE
CERTIFICATE OF CORRECTION

PATENT NO. : 6,819,785 B1
DATED : November 16, 2004
INVENTOR(S) : Vining et al.

It is certified that error appears in the above-identified patent and that said Letters Patent is hereby corrected as shown below:

Column 17,
Line 7, after "finding of the" delete the word "set".

Signed and Sealed this

Twenty-second Day of February, 2005

JON W. DUDAS
*Director of the United States Patent and Trademark Office*